United States Patent [19]

Craig et al.

[11] Patent Number: Plant 7,656

[45] Date of Patent: Sep. 24, 1991

[54] REGAL PELARGONIUM '315-(83-48-1)'

[75] Inventors: Richard Craig, State College, Pa.; Glenn G. Hanniford, Worthington, Ohio

[73] Assignee: Research Corporation Technologies, Inc., Tuscon, Ariz.

[21] Appl. No.: 383,958

[22] Filed: Jul. 21, 1989

[51] Int. Cl.[5] ..... A01H 5/00
[52] U.S. Cl. ..... Plt./68
[58] Field of Search ..... Plt./68

*Primary Examiner*—Howard J. Locker
*Attorney, Agent, or Firm*—Scully, Scott, Murphy & Presser

[57] ABSTRACT

This invention relates to a new and distinct cultivar of regal Pelargonium (*Pelargonium*×*domesticum*) named 'Splendor' substantially as illustrated and described herein, particularly characterized as being compact and self-branching, early flowering and floriferous, and having bright salmon pink flowers with ruby feathering on the upper petals.

2 Drawing Sheets

The present invention relates to a new and distinct cultivar of regal Pelargonium (*Pelargonium*×*domesticum*) called 'Splendor'. This cultivar is characterized as being compact and self-branching (without pinching), early flowering and floriferous. The ruffled flowers are bright salmon pink with ruby feathering on the upper petals.

The cultivar was developed from an organized, scientifically designed breeding program conducted at the Department of Horticulture, The Pennsylvania State University, University Park, Pa. 16802. The objective was to produce a new regal pelargonium genotype with excellent propagation characteristics, compact growth habit, predictable and consistent flowering response, and acceptable postharvest quality. The pedigree of this cultivar is as follows:

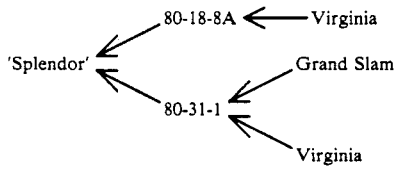

'Splensor' includes the cultivars 'Virginia' and 'Grand Slam' in its ancestry. It resembles but is much lighter than 'Virginia' in its flower color; however, it is a smaller, more compact plant with improved branching characteristics and it flowers earlier under low irradiance conditions. 'Splendor' produces twice as many flowers as 'Grand Slam' and is much more amenable to flowering under warm temperature conditions.

The selection was asexually propagated by cuttings and the reproductions ran true.

Figure 1:
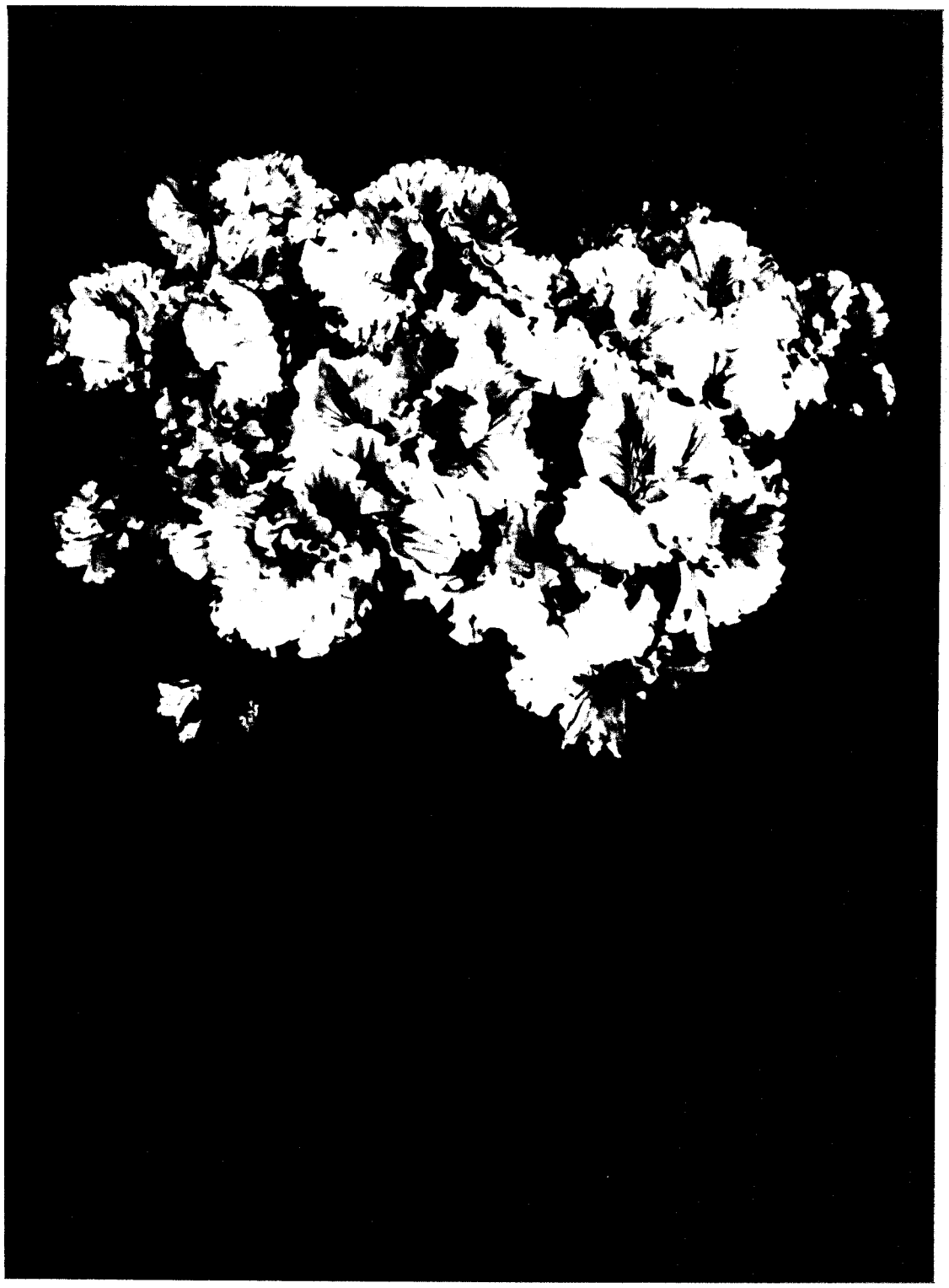
FIG. 1 illustrates in color the cultivar including foliage and flowers.
Figure 2:
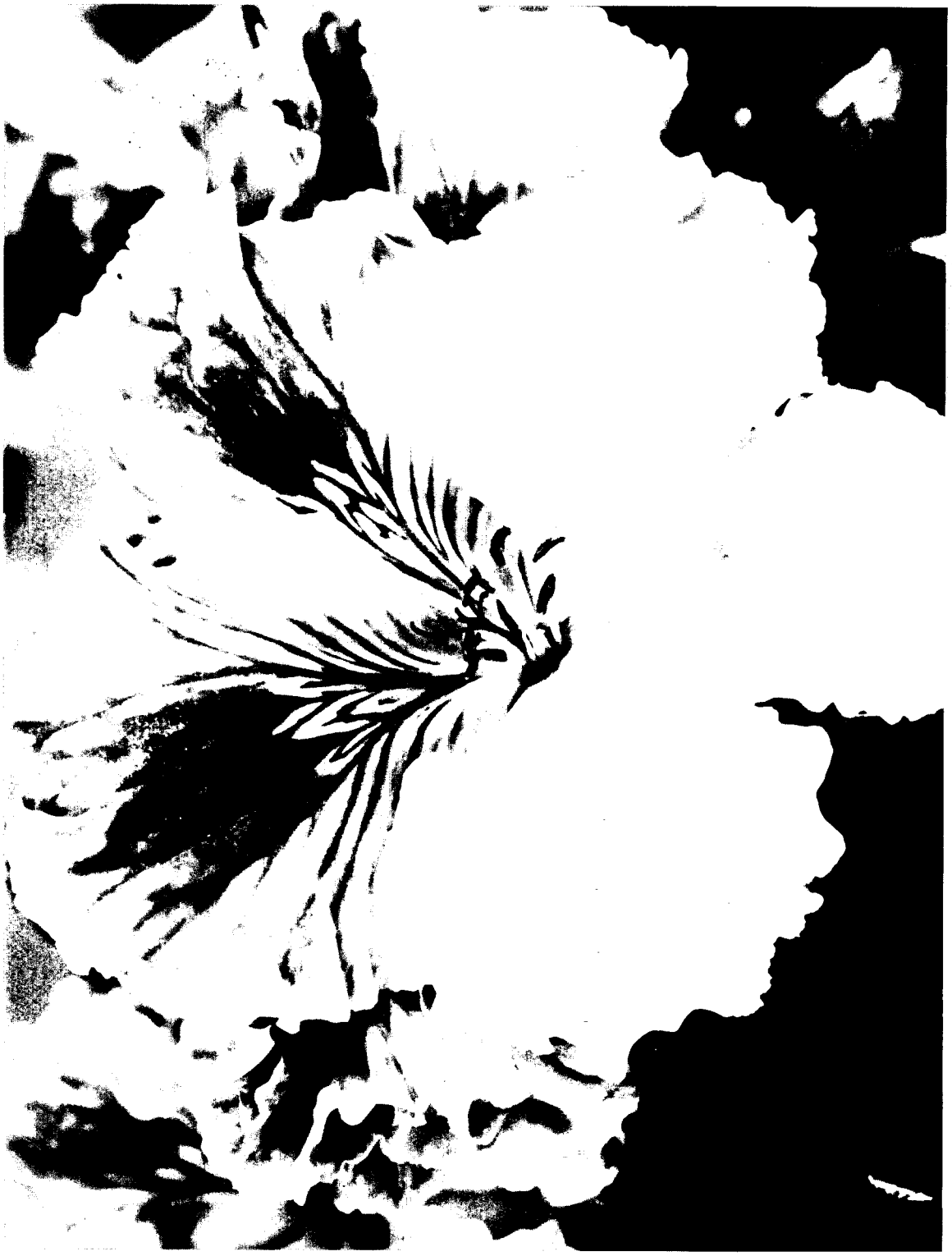
FIG. 2 illustrates in color primarily the floret.

With reference to the detailed description of the cultivar which follows, the test plant was potted in soilless medium and grown in a glasshouse under natural sunlight, at a night temperature of approximately 58° F. and a day temperature of approximately 68° F. Fertilizer was applied in every watering with 200 ppm nitrogen provided in the forms of 15-16-17 (two consecutive waterings) and 20-0-20 (every third watering) in a repeating cycle.

Color readings were taken under daylight fluorescent light at approximately 200 foot candles and color identification was by reference to the Royal Horticultural Society Colour Charts, except where common terms of color definition are employed.

THE PLANT

Classification:
- *Botanical.*—*Pelargonium*×*domesticum.*
- *Tradename.*—Splendor.

Form: Compact, self-branching.

Height: Approximately 21.0 cm to top of plant canopy [will vary with environmental and cultural conditions].

Leaves:
- *Size.*—Largest leaf measured 8.0 cm long×10.0 cm wide.
- *Shape.*—Depressed ovate; base is cuneate to truncate to reniform; variously lobed; ratio of length to width is 2 to 3.
- *Margin.*—Toothed.
- *Texture.*—Pubescent.
- *Color.*—Adaxial: Green 137C. Abaxial: Green 137B.
- *Ribs and veins.*—Palmate venation.
- *Petioles.*—Texture: Lightly pubescent. Length: 6.0 to 8.5 cm. Color: Yellow-green 144A.

Stem:
- *Internode length.*—2.0 to 4.0 cm.
- *Color.*—Yellow-green 144A.

THE FLOWER

Blooming habit: Early and moderately floriferous, often comparable in earliness and inflorescence number to the cultivar 'Parisienne'.

Inflorescence form: Umbellate.

Inflorescence size: Varies with floret number; often 8.0–12.0 cm across (with florets fully open).

Disease resistance: Not known.

Florets:
- *Number.*—4 to 5 per inflorescence.
- *Form.*—Cupped.
- *Size.*—5.0–7.0 cm across open floret.

Petals:

*Number.*—5–6.

*Texture and appearance.*—Smooth, with slightly ruffled edges.

*Color.*—Upper petals: Adaxial: Margin: White. Central spot: Red-purple 59A on a background of red 40A mixed with white 155D. Proximal veins and feathering: Red-purple 59A and red 52A. Abaxial: White with red 52A feathering. Lower petals: Adaxial: Mostly red-purple 62C background with slightly darker streaks (red-purple 62A); sometimes with white 155B background with red-purple 62A and 62C patches. Abaxial: White with slight red 52B feathering.

Petaloids:

*Number.*—0, 1 or 2.

*Shape.*—Petal-like (sometimes fused with a sepal).

*Color.*—Similar to the color of the petals.

Sepals:

*Number.*—5–6.

Pedicel: Subtended by bracts.

*Length.*—2.4 to 3.3 cm.

*Color.*—Yellow-green 144A.

Peduncle: Arises from node; opposed to leaf petiole; subtended by leaves and bracts.

*Length.*—8.3 cm.

*Color.*—Yellow-green 144A.

REPRODUCTIVE ORGANS

Androecium:

*Stamens.*—7–8 flat, ribbon-like filaments, joined at their bases; upper ⅓ of filaments is light purple; versatile attachment to anthers which are light purple and well developed with thinner extension at tip, 2 sizes of orange pollen.

*Staminodes.*—2–3 flat, ribbon-like filaments with no anthers.

*Petaloid stamens.*—None observed.

Gynoecium:

*Pistil number.*—1.

*Length.*—12.0–19.5 mm.

*Stigma.*—5–6-parted; purple.

*Style.*—3.5–11.5 mm long; purple.

*Ovary.*—3.5–6.5 mm long; superior; very pubescent.

*Fruit.*—Schizocarp; rarely observed.

What is claimed is:

1. A new and distinct cultivar of regal Pelargonium substantially as illustrated and described herein, particularly characterized as being compact and self-branching, early flowering and floriferous, and having bright salmon pink flowers with ruby feathering on the upper petals.

* * * * *